(12) United States Patent
Gabriel

(10) Patent No.: US 6,870,479 B2
(45) Date of Patent: Mar. 22, 2005

(54) WETNESS MONITORING SYSTEM FOR TRACKING WETNESS EVENTS IN DIAPERS

(76) Inventor: Michael Lynn Gabriel, 30 S. El Camino Real, #104, San Mateo, CA (US) 94401

( * ) Notice: Subject to any disclaimer, the term of this patent is extended or adjusted under 35 U.S.C. 154(b) by 47 days.

(21) Appl. No.: 10/306,961

(22) Filed: Nov. 29, 2002

(65) Prior Publication Data

US 2003/0137425 A1 Jul. 24, 2003

Related U.S. Application Data

(60) Provisional application No. 60/337,189, filed on Dec. 1, 2001.

(51) Int. Cl.⁷ ............................................. G08B 21/00
(52) U.S. Cl. ................. 340/604; 340/573.5; 340/573.1; 200/61.05; 200/182
(58) Field of Search ............................ 340/604–573.5; 200/182, 61.04, 61.05, 61.06

(56) References Cited

U.S. PATENT DOCUMENTS

| | | | |
|---|---|---|---|
| 4,163,449 A | * | 8/1979 | Regal ........................ 128/886 |
| 4,977,906 A | * | 12/1990 | Di Scipio ................... 128/885 |
| 5,459,452 A | | 10/1995 | DePonte |
| 5,903,222 A | | 5/1999 | Kawarizadeh et al. |
| 6,384,728 B1 | * | 5/2002 | Kanor et al. ............. 340/573.1 |
| 6,407,308 B1 | * | 6/2002 | Roe et al. ................... 604/361 |
| 6,603,403 B2 | * | 8/2003 | Jeutter et al. ............... 340/604 |
| 2002/0003478 A1 | * | 1/2002 | Zhao et al. .............. 340/573.1 |

* cited by examiner

Primary Examiner—Jeffery Hofsass
Assistant Examiner—Eric Blount
(74) Attorney, Agent, or Firm—The Maxham Firm

(57) ABSTRACT

A personal care monitoring system is disclosed. In accordance with one embodiment, the monitoring system may include a wetness sensor configured to detect a wetness event occurring within an associated diaper, and a human life sensor configured to detect presence of human life relative to the associated diaper. A monitoring unit having a system controller in communication with the wetness and human life sensors may be utilized in such a manner that the system controller monitors the wetness and human life sensors and generates data associated with detected wetness events and presence of human life relative to the associated diaper.

37 Claims, 12 Drawing Sheets

Personal Care Event Log

| | 1 | 2 | 3 | ... | N |
|---|---|---|---|---|---|
| Base Start Time | 8:00 A.M. | 8:00 A.M. | 8:00 A.M. | ... | ... |
| Wetness Event Number | One | Two | Three | ... | N |
| Wetness Detected | 9:15 A.M. | 10:12 A.M. | 11:42 A.M. | ... | ... |
| Wetness End Time (diaper off) | 9:35 A.M. | 10:18 A.M. | 1:48 P.M. | ... | ... |
| Elapsed Wet Time | 20 Min. | 6 Min. | 126 Min. | ... | ... |
| Diaper Replaced | 9:45 A.M. | 10:23 A.M. | 1:55 P.M. | ... | ... |
| Elapsed Diaper Off | 10 Min. | 5 Min. | 7 Min. | ... | ... |

FIG. 7

WETNESS MONITORING SYSTEM FOR TRACKING WETNESS EVENTS IN DIAPERS

CROSS REFERENCE TO RELATED APPLICATIONS

This application claims benefit of priority from U.S. Provisional Patent Application Ser. No. 60/337,189, entitled "Diaper Wetness Monitoring System" filed Dec. 1, 2001, the entire disclosure of which is incorporated herein by reference for all purposes.

BACKGROUND OF THE INVENTION

1. Field of the Invention

The present invention relates generally to a wetness monitoring system, and in particular, to a wetness monitoring system that permits qualitative assessment of provided care.

2. Description of the Related Art

An assortment of wetness detecting systems and associated devices have been previously proposed and implemented to monitor the condition of a diaper, bedding, adult incontinence brief, and other similar articles. The general principle of many wetness detection systems is to implement some sort of urine or wetness detector in cooperation with a display or alarm device. Some systems activate an audible or visible alarm to indicate the presence of urine within the diaper. This is typically accomplished by the detection of some threshold wetness level within a diaper.

Concerned parents have increasingly desired to know whether or not their infant or infirm adult has been subjected to excessive time in a wet diaper, for example, because of a dilatory caregiver. This information is often helpful to permit a parent or guardian, for example, to qualitatively assess care provided by a caregiver to an infant or infirm adult. In an apparent response to these needs, some systems purport to track and record the timing and frequency of urinating events and associated diaper changes.

A common problem encountered by many existing wetness detector systems is a susceptibility to system tampering and data manipulation by a less than scrupulous caregiver. For example, some systems may be easily disconnected from the infant's diaper and simply tossed aside by a caregiver in anticipation of improper or negligent care.

While there have been some attempts at implementing wetness monitoring systems that permit qualitative assessment of care provided by a caregiver, for example, these attempts have met with varying levels of success and improvement is still needed.

SUMMARY OF THE INVENTION

A personal care monitoring system according to one embodiment includes a wetness sensor configured to detect a wetness event occurring within an associated diaper, and a human life sensor configured to detect presence of human life relative to the diaper. A monitoring unit having a system controller in communication with the wetness and human life sensors may be utilized in such a manner that the system controller monitors the wetness and human life sensors and generates data associated with detected wetness events and detected presence of human life relative to the diaper.

These and other aspects, features and advantages of the present invention will become more apparent upon consideration of the following description of preferred embodiments taken in conjunction with the accompanying drawings, in which like reference numerals designate like parts throughout.

BRIEF DESCRIPTION OF THE DRAWINGS

FIG. 7 is an example of the types of data that may be acquired and provided in accordance with the invention;

DETAILED DESCRIPTION OF THE PREFERRED EMBODIMENTS

Figure 1A:
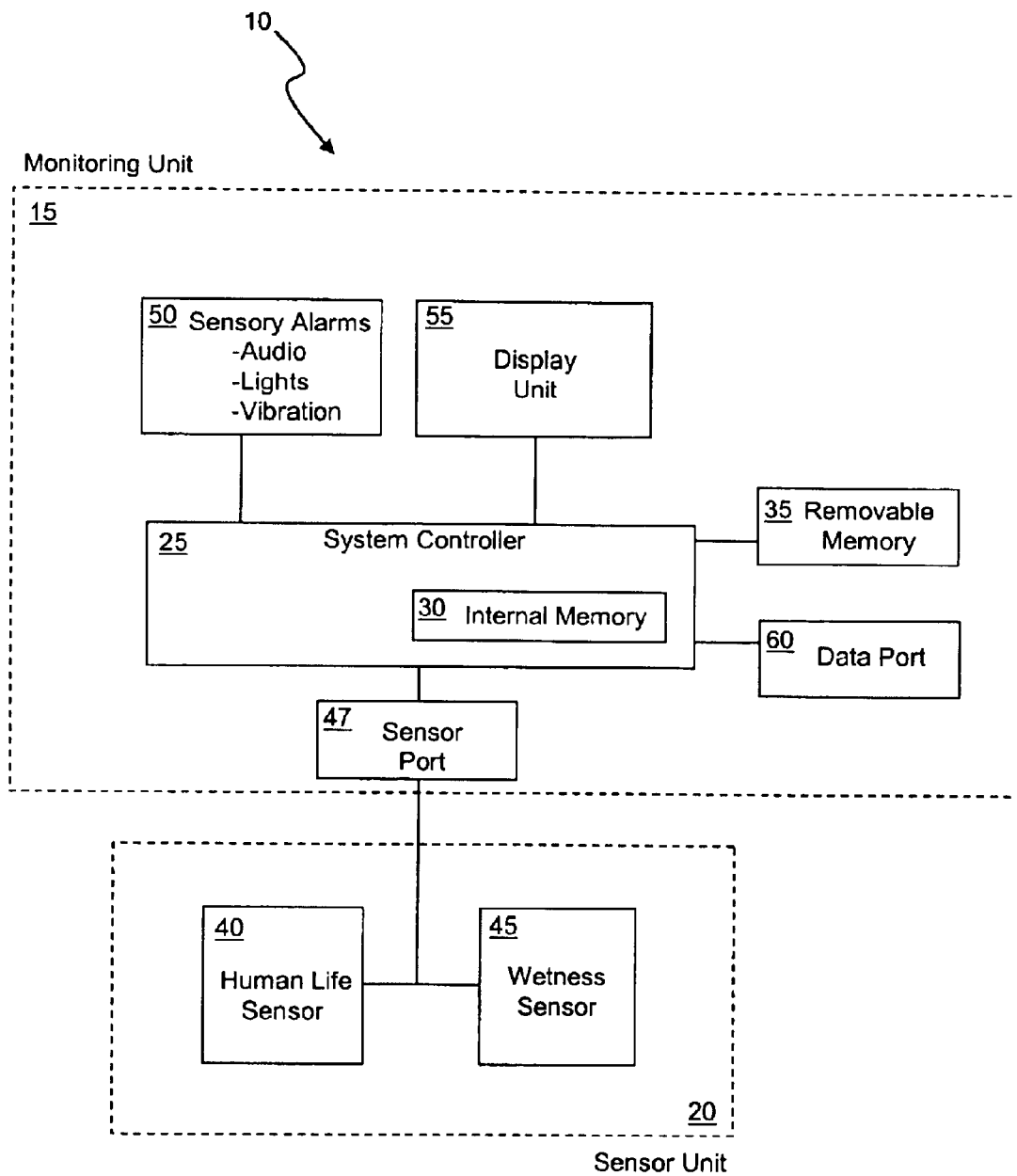
FIG. 1A is a block diagram showing one embodiment of the present invention.

In the following description of preferred embodiments, reference is made to the accompanying drawings, which form a part hereof, and which show by way of illustration, specific embodiments of the invention. It is to be understood by those of working skill in this technological field that other embodiments may be utilized, and structural, electrical, as well as procedural changes may be made without departing from the scope of the present invention.

The terms "wetness" and "wetness event" are to be understood as including human urination, defecation, and other bodily discharge events. Furthermore, the term "diaper" as used herein refers to disposable and reusable devices which absorb and contain a wetness event and may include diapers, pants-type diapers, training pants, and adult incontinence briefs which are widely used in the care of infants, toddlers, and incontinent adults.

It is to be understood that a personal care monitoring system and associated methods of the present invention are applicable to a wide variety of situations where the qualitative monitoring of provided care is desired. Although several implementations will be discussed in the context of the invention configured with an infant diaper, it will be appreciated that slight modifications of the system may make it even more applicable to other systems and care giving situations without the need of inventive faculty.

Referring now to FIG. 1, a block diagram of one embodiment of the present invention is shown and generally designated 10. As shown, monitoring system 10 generally includes a monitoring unit 15 and a sensor unit 20. Control of some or all of the monitoring and sensor units 15, 20 may be provided by an appropriate processing device, such as system controller 25.

System controller 25 may include a microprocessor, microcontroller, application specific integrated circuit (ASIC), embedded processor, or any other suitable control or processing device. Controller 25 is typically configured with appropriate memory for processing, recording, and storing data relating to personal care monitoring of an individual. For example, controller 25 may be configured with internal memory 30 or removable memory 35, or both. Internal and removable memory 30, 35 may be any type or combination of any suitable volatile or non-volatile memory device such as random access memory (RAM), electrically erasable programmable read-only memory (EEPROM), erasable programmable read-only memory (EPROM), programmable read-only memory (PROM), read-only memory (ROM), magnetic memory, flash memory, or other similar memories. Data obtained in accordance with the invention will be collectively referred to as personal care data, and may be stored using any of the just-described memory devices using any suitable technique.

The monitoring unit 15 is shown in communication with the sensor unit 20 which typically comprises a human life sensor 40 and a wetness sensor 45. A sensor port 47 may be used to facilitate an electronic coupling between the monitoring and sensor units 15, 20. Typically, the sensor port 47 provides a detachable coupling between components, but hardwired configurations are possible if so desired. According to some embodiments, the invention may be implemented by positioning sensor unit 20 within a diaper (not shown in this Figure), while the monitoring unit 15 is attached to the outside of the diaper; however, many other configurations are possible and will be described in more detail herein.

Life sensor 40 may include any suitable device which can detect human presence and/or absence. For example, life sensor 40 may be configured as a heat sensor, salinity sensor, heart rate monitor, conductance device, pH measuring device, and the like. Regardless of the type of sensor implemented, instances of human presence and/or absence relative to an associated diaper may be ascertained and is useful for implementing an anti-cheat feature, as will be described in more detail herein.

In general, wetness sensor 45 may include any appropriate device operable with the invention and which can detect a wetness event. Sensor variations include devices that can detect threshold levels of, for example, hydrogen ion (OH—), urea, pH, ammonia, and the like. In one implementation, the wetness sensor may generate a signal whenever a threshold level of wetness has occurred, thus indicating an occurrence of a wetness event.

Alternatively, a wetness sensor that generates a continuous signal that indicates that some threshold level of wetness has not been reached may also be used. In this implementation, a wetness event may be detected whenever the wetness sensor has not generated a signal for some predetermined time interval.

Sensors 40 and 45 may be implemented in any of a variety of different manners. For instance, these sensors may be formed as a fine wire mesh or as one or more discrete sensor devices appropriately placed within or on a diaper. Regardless of which type of sensor design utilized, sensors 40 and 45 may be insertable or embedded within an associated diaper. An embedded sensor configuration is typically utilized in conjunction with disposable diapers, whereas an insertable design may be used with disposable, and reusable (e.g., cloth) diapers. Sensors 40 and 45 are shown as discrete components; however, the invention is not so limited and other designs can be utilized where the functionality of these sensors is integrated into a single sensor, if desired.

Typically, communication between the monitoring unit 15 and the sensor unit 20 is accomplished via hardwired electrical components. However, some or all of the communications between these components may be accomplished, if desired, using other signaling technologies such as radio frequencies (RF), infrared (IR), and the like.

Monitoring unit 15 may be optionally configured with any of a variety of devices to facilitate the monitoring of personal care. For example, the monitoring unit 15 may include one or more sensory alarms 50, a display unit 55, and a data port 60. Sensory alarms 50 are typically utilized to alert a caregiver, for example, that a wetness event has occurred. Typical sensory alarms include auditory alarms, visual indicators such as light-emitting diodes (LED), vibration devices, and the like. A display unit 55 may be utilized to view and recall information associated with the personal care of the person (e.g., infant or incontinent adult) utilizing the device. For example, an appropriate display unit 55 may provide the time, frequency, and duration of a wetness event, as well as the time and elapsed duration of diaper replacement. Appropriately configured systems can record and provide data for a number of wetness events, which is useful for monitoring personal care over an entire day, week, month, or other desired monitoring periods.

In some implementations, the monitoring unit 15 may be configured with a suitable data port 60 to facilitate data communications. The inclusion of a data port 60 enables a user to access and view data obtained during one or more personal care monitoring periods using an appropriately equipped device such as a general or specific purpose computer. Data port 60 may be formed using any suitable device such as a serial port, universal serial bus (USB), and the like.

Figure 1B:
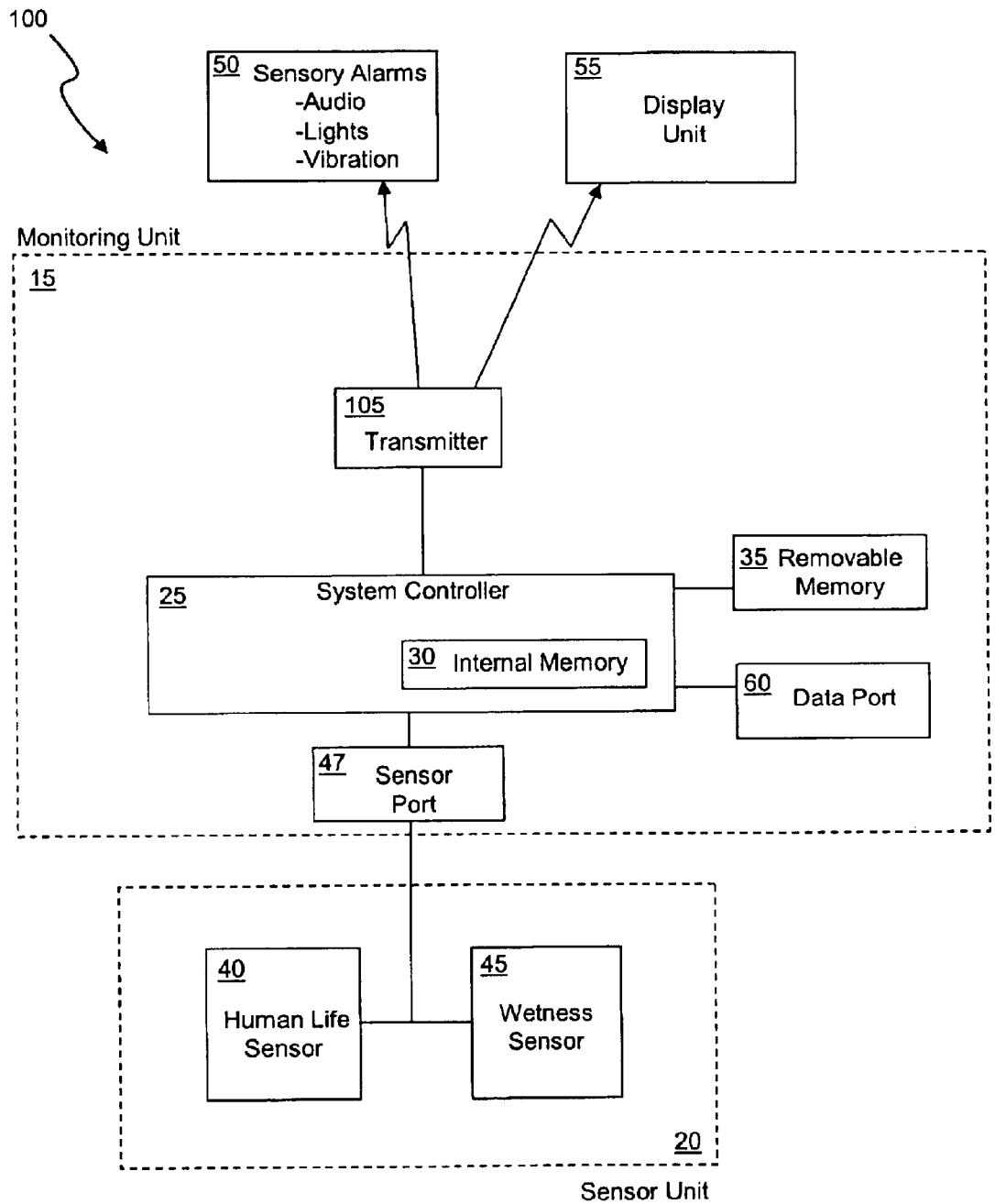
FIG. 1B is a block diagram showing an alternative embodiment of the present invention.

FIG. 1B is a block diagram of an alternative embodiment of the present invention, generally designated 100. Similar to other embodiments, monitoring system 100 generally includes monitoring and sensor units 15, 20. However, in the illustrated embodiment, the monitoring unit 15 is configured with a transmitter 105 to support wireless communications between the unit 15 and externally configured components such as sensory alarms 50 and/or display unit 55. Wireless communication may be accomplished using any suitable signaling technology (e.g., RF, IR, etc.) The monitoring unit 15 may also be configured with removable memory 35 and/or a data port 60, if desired.

Figure 1C:
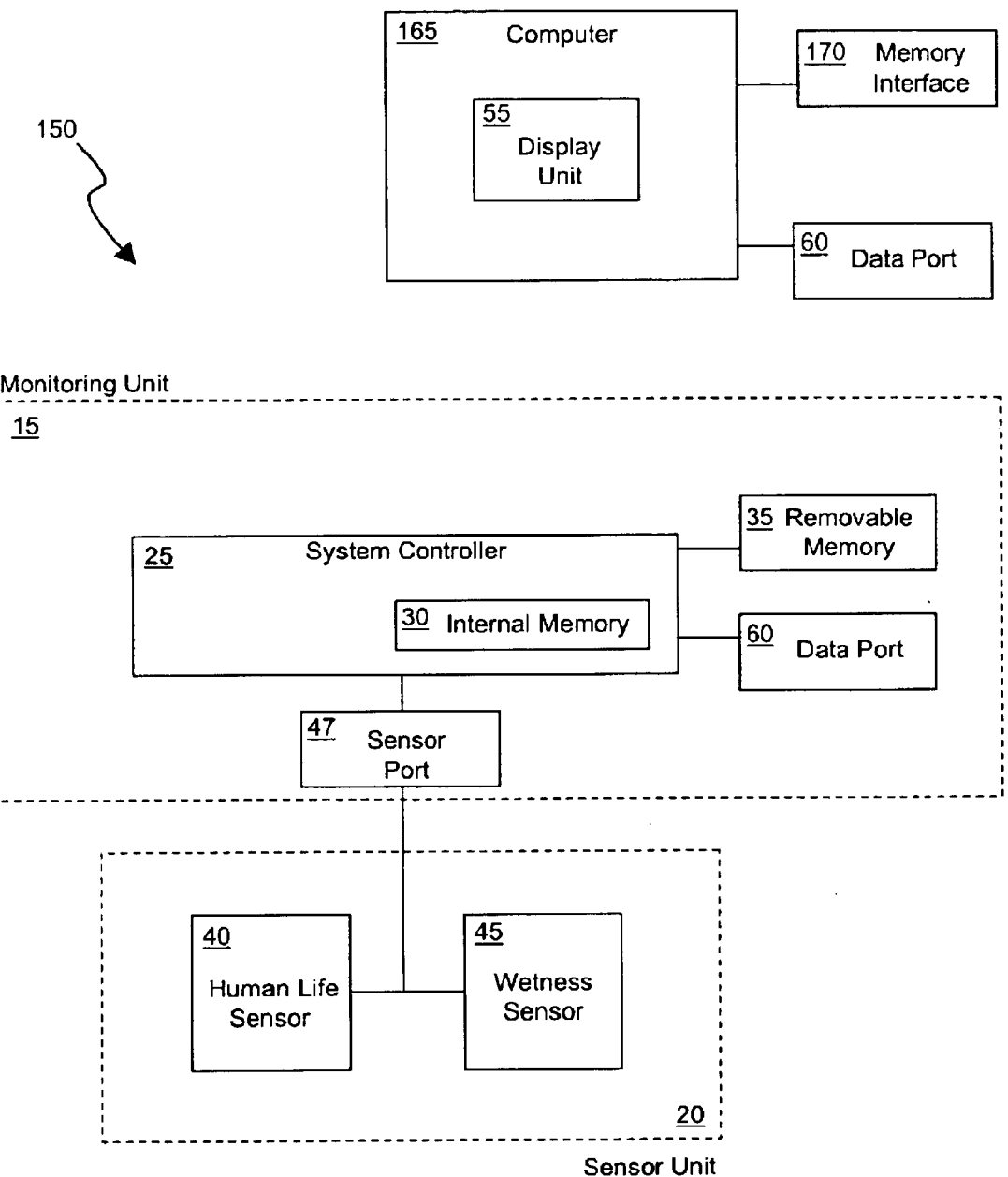
FIG. 1C is a block diagram showing another alternative embodiment of the present invention.

FIG. 1C is a block diagram of another alternative embodiment of the present invention, generally designated 150. Often, a personal care monitoring system may be utilized to monitor care provided by a caregiver to an infant or infirm adult. In these instances, it may not be necessary or even desirable to enable a caregiver an opportunity to view or access data obtained by the system. To accommodate these needs, a monitoring unit 15 may be implemented without an attached or integrated display unit. In these configurations, the monitoring unit 15 may be outfitted with devices, such as removable memory 35 and/or data port 60, to enable authorized persons (e.g. parents and guardians) an ability to view data obtained during one or more personal care monitoring periods.

FIG. 1C further shows a generalized example of an external display system that may be used in conjunction with monitoring and sensor units 15, 20. As shown, the external display system includes a computer 165 having a display 55 and optional features such as a memory interface 170 and data port 60.

Computer 165 may be any suitable computational device which permits viewing of data obtained in accordance with the invention. As used herein, a "computational device" includes, but is not limited to, personal computers (PC) having an operating system such as DOS, Windows™, OS/2™ or Linux™; Macintosh™ computers; computers having JAVA™ OS as the operating system; graphical workstations such as the computers of Sun Microsystems™ and Silicon Graphics™, and other computers having some version of the UNIX operating system such as AIX™ or SOLARIS™ of Sun Microsystems™; or any other known and available operating system, or any device, including but not limited to: laptops, hand-held computers, personal data assistant (PDA) devices, cellular telephones, any type of wireless application protocol (WAP) or short message service (SMS) enabled device, and wearable computers of any sort.

Display 55 may be any suitable display device operable with any of the computing devices described herein. The optional data port 60 may include any suitable device supporting data communications between the monitoring unit 15 and the computer 165 (e.g., a serial port, universal serial bus (USB), and the like). Similarly, memory interface 170 may be any of a variety of appropriate devices and/or interfaces permitting data retrieval from removable memory 35.

Figure 2:
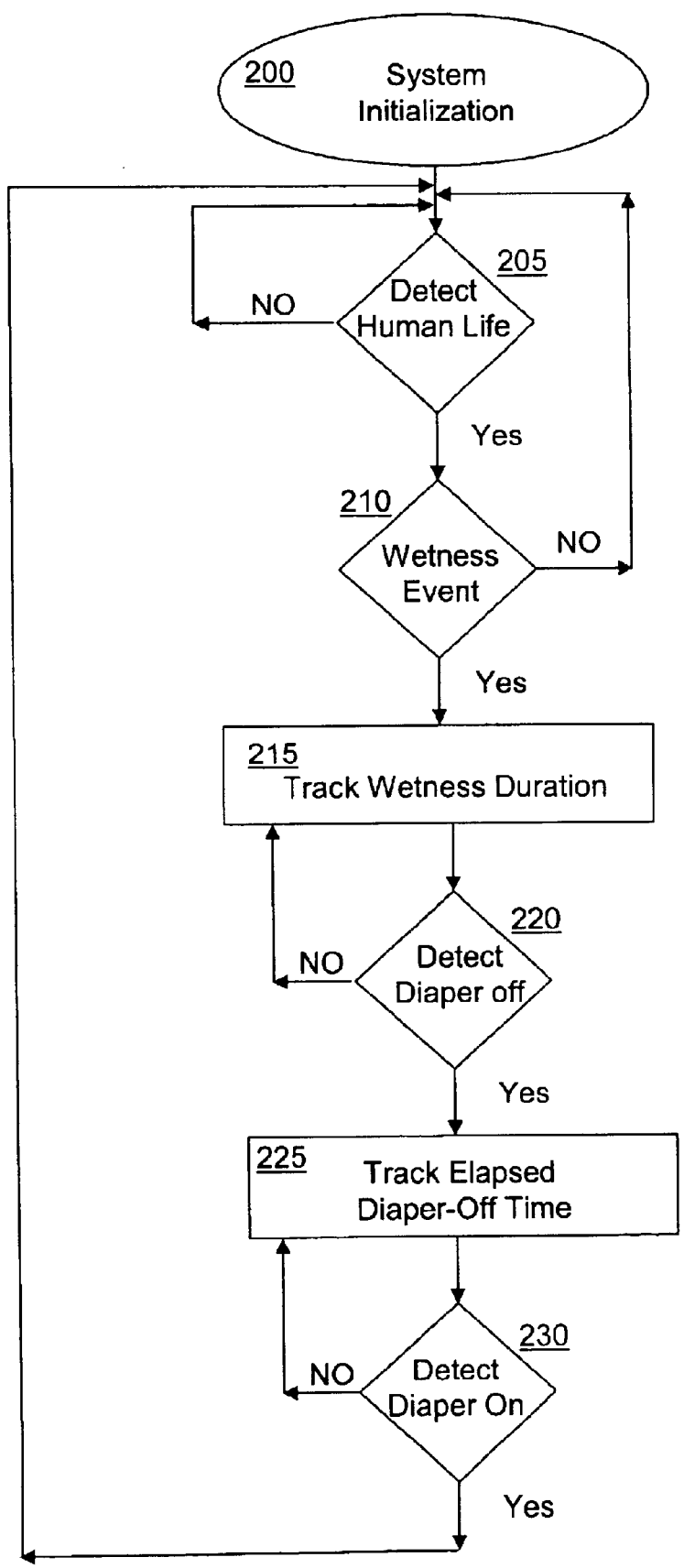
FIG. 2 is a flowchart showing exemplary operations for implementing a personal care monitoring system according to some embodiments of the present invention.

FIG. 2 is a flowchart showing exemplary operations for implementing a personal care monitoring system according to some embodiments of the present invention and will be described with occasional reference to system 10 shown in FIG. 1A.

By way of example only, the following description of data acquisition in accordance with the invention will reference the following generalized scenario. A parent has outfitted their infant with diapers equipped with a personal care monitoring system in accordance with an embodiment of the invention. The parent leaves the infant in the custody of a caregiver who provides care over a period of a single day.

As indicated at Block 200, the system may undergo an initialization procedure where routine or necessary procedures are executed or performed as may be required for proper operation. Typical procedures include system checks, memory allocations, initialization of various system settings. In some embodiments, the initialization procedure will verify that a user is authorized to use or access the system. This verification operation may utilize, for example, a user pass code or other similar user authentication method.

After initialization, control may flow to a human life detection operation, as indicated in Block 205. This operation may be accomplished using, for example, the human life sensor 40. If no human life is detected (e.g., a diaper is not properly placed on the infant), then the time and occurrence of this event may be recorded in the personal care event log, for example, and control may flow back to block 205 to complete an inner loop that continuously or periodically checks for human life. On the other hand, if the presence of human life is detected (e.g., a diaper is appropriately placed on the infant), then the time and occurrence of this event may be recorded in the personal care event log, for example, and control may flow to a wetness event detection operation, as indicated in Block 210.

A wetness event detection operation may be accomplished using, for example, the wetness sensor 45. If a wetness event is not detected, then control may flow back to block 205 to complete an inner loop that continuously or periodically checks for a wetness event, as well as for the presence of human life (e.g. to detect any instances of diaper removal prior to detection of a wetness event). On the other hand, if a wetness event is detected, then the time and occurrence of this event may be recorded in the personal care event log, for example, and control may flow to Block 215 where the wetness duration may be tracked (e.g., the elapsed time that the infant is in contact with a wet diaper). If desired, one or more sensory alarms may also be activated to signal a caregiver of the wetness event.

Tracking the wetness duration is useful to provide parents or guardians with information as to the amount time their infant remains in a wet diaper. Excessive time in a wet diaper may indicate an inattentive or even negligent caregiver.

Control may then flow to a human life detection operation, as indicated in Block 220. If the presence of human life is detected (e.g., the infant continues to have a wet diaper), then control may flow back to Block 215 so that the wetness duration may be continued to be tracked. This operation completes an inner loop that continuously or periodically checks for human life. On the other hand, if no human life is detected (e.g., a diaper change is in progress), then the time and occurrence of this event may be recorded in the personal care event log, for example, and control may flow to Block 225 where the diaper off duration may be tracked (e.g., the elapsed time that the infant does not have a diaper).

Tracking the diaper off duration is useful to provide parents or guardians with information as to the amount time their infant remains without a diaper. Excessive time without a diaper may indicate an inattentive or negligent caregiver, or a caregiver who may be attempting to conceal dilatory actions.

Control may then flow to another human life detection operation, as indicated in Block 230. If no human life is detected (e.g., a "new" diaper has not yet been placed on the infant), then control may flow back to Block 225 where the diaper off duration may be tracked (e.g., the elapsed time that the infant does not have a diaper). This operation completes an inner loop that continuously or periodically checks for human life. On the other hand, if the presence of human life is detected (e.g., a diaper is appropriately placed on the infant), then the time and occurrence of this event may be recorded in the personal care event log, for example, and control may flow to Block 205 where the just-described operations may be repeated. Notably, each iteration of the operations shown in this flowchart may be associated with a single wetness event. Accordingly, data associated with a plurality of wetness events may obtained using the illustrated (or other similar) operations.

It is to be understood that in many embodiments, the system performs periodic or continuous checks for human life. This feature not only enables a parent, for example, to track the changing of the infant's diaper, but also provides a mechanism for preventing system tampering or manipulation by a caregiver attempting to conceal negligent care.

Although the present invention may be implemented using the exemplary series of operations shown in FIG. 2, those of ordinary skill in the art will realize that additional or fewer operations may be performed. Moreover, it is to be understood that the order of operations shown in FIG. 2 is merely exemplary and that no single order of operation is required or necessary.

Figure 3A:
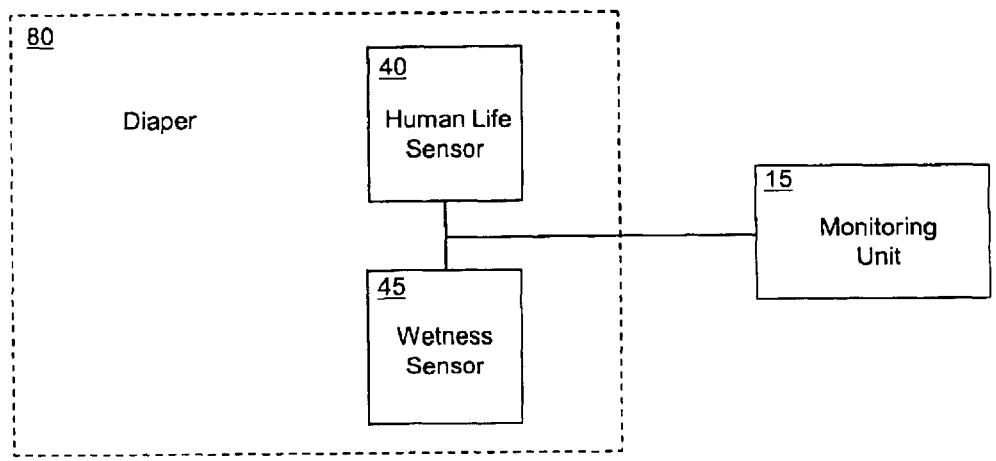
FIGS. 3A and 3B are block diagrams showing some of the many configurations possible for implementing the present invention.
Figure 3B:
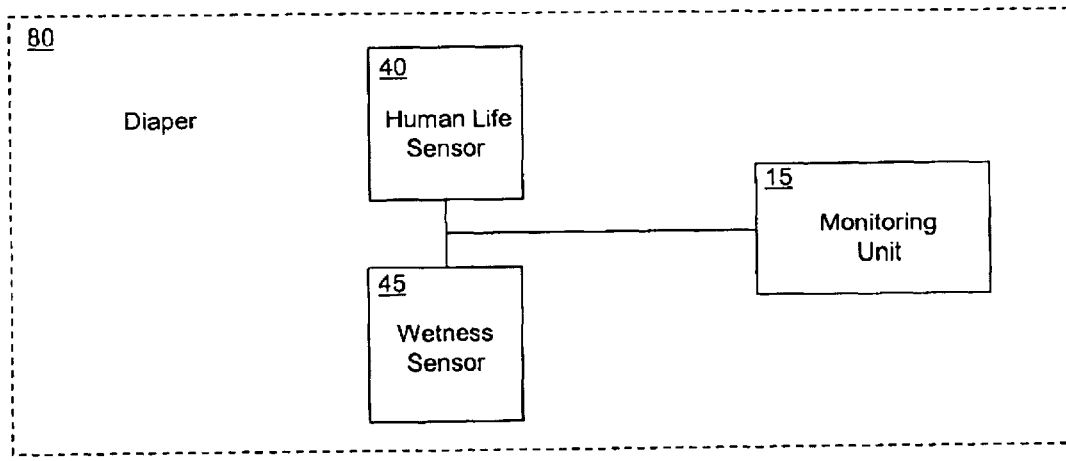

FIGS. 3A and 3B are block diagrams showing some of the many configurations possible for implementing the present invention. In particular, FIG. 3A depicts a disposable or reusable diaper 80 having human life and wetness sensors 40, 45 which are in communication with a monitoring unit 15.

In some embodiments, sensors 40, 45 may be manufactured as low-cost disposable devices, while in other embodiments these sensors are reusable. Similarly, monitoring unit 15 can be fabricated as a disposable or reusable device to accommodate a user's particular need. Because these sensors and monitoring units may be configured to cooperate with disposable and reusable (e.g., cloth) diapers, a wide variety of implementations are possible. Accordingly, the present invention may be implemented using any combination of disposable/reusable sensors, monitoring units, and diapers.

For example, in a completely disposable implementation, diaper 80 may be fabricated having disposable human life and wetness sensors 40, 45, and configurable with a disposable monitoring unit 15. In these configurations, the monitoring unit 15 may be attached (or attachable) to the sensors 40, 45 in a manner depicted in FIG. 3A. Alternatively, as shown in FIG. 3B, the monitoring unit 15 may be completely integrated with the diaper 80. Completely integrated embodiments often include removable memory 35 so that personal care data may be retrieved by, for example, a parent or guardian. Other disposable embodiments include disposable sensors 40, 45 fabricated as discrete components adaptable to any of variety of diaper types. These implementations are useful when personal care monitoring is desired using readily available, off-the-shelf diapers.

Figure 4A:
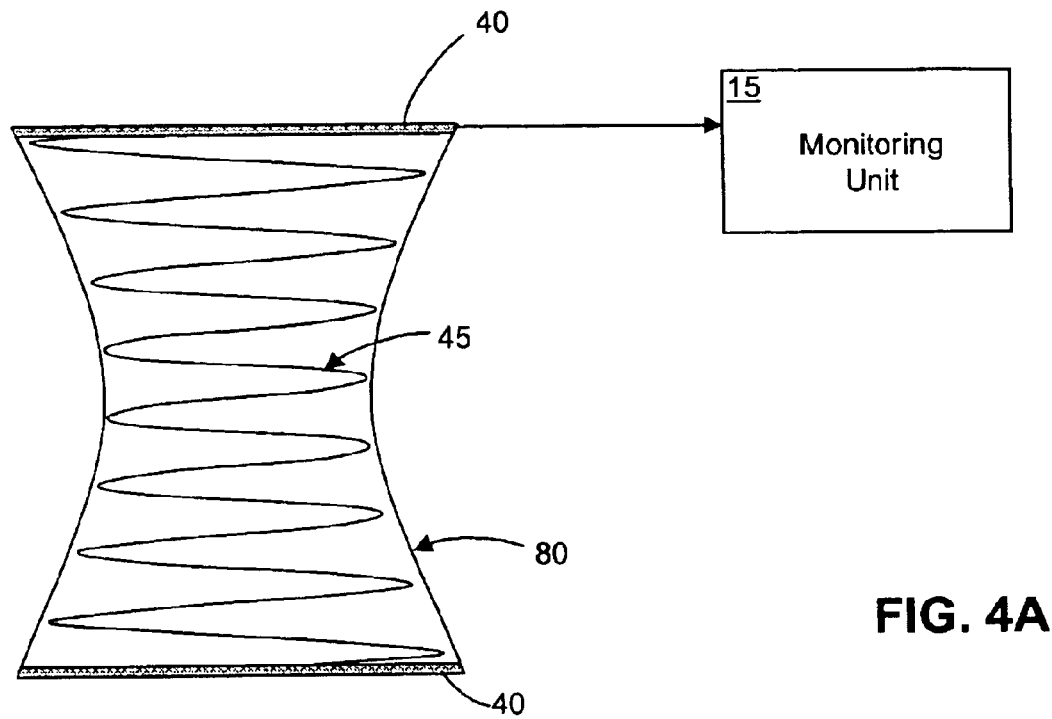
FIGS. 4A and 4B are more detailed views of possible sensor implementations according to some embodiments of the present invention.
Figure 4B:
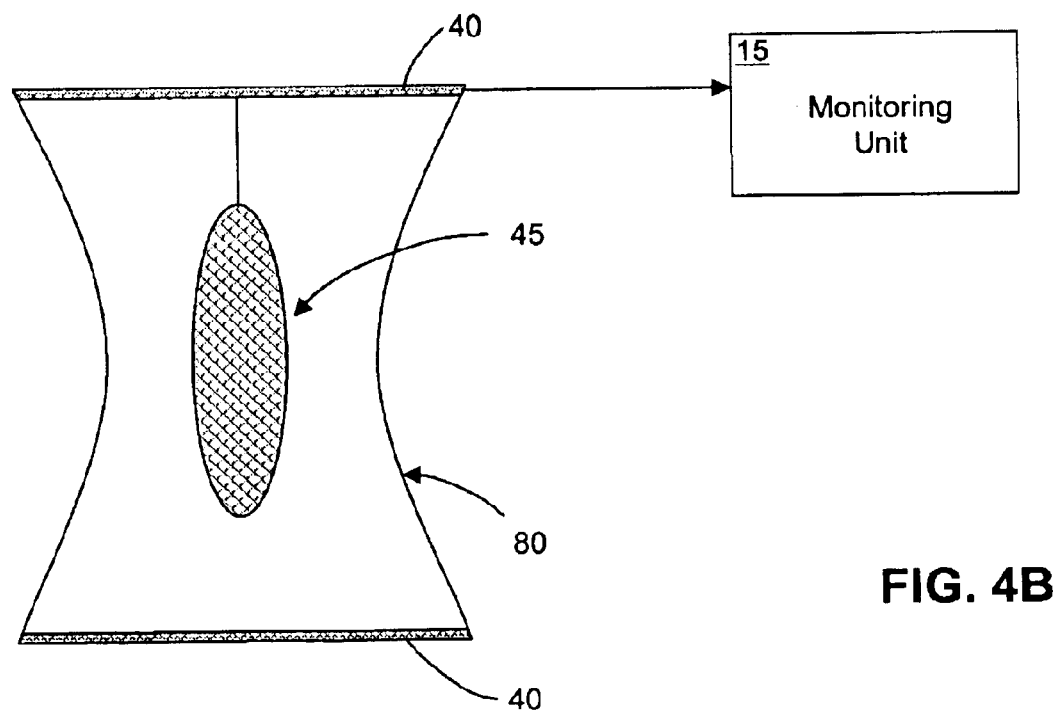

FIGS. 4A and 4B are more detailed views of possible sensor implementations according to some embodiments of the invention. For example, FIG. 4A depicts a diaper 80 configured with a wire mesh wetness sensor 45. In this example, a human life sensor 40 may be positioned at opposing ends of the diaper 80. Although the wire mesh wetness sensor 45 may be disposed on (or integrated within) a portion of the diaper 80, the exact positioning or size of the sensor is not critical to the invention. For example, FIG. 4B shows still another alternative design where the wetness sensor 45 occupies a centralized portion of the diaper 80. This centralized portion is often associated with the portion of a diaper most likely to experience a wetness event. It is therefore to be understood that the invention may be implemented using any of a variety of different sensor configurations, sizes, and geometries.

Figure 5:
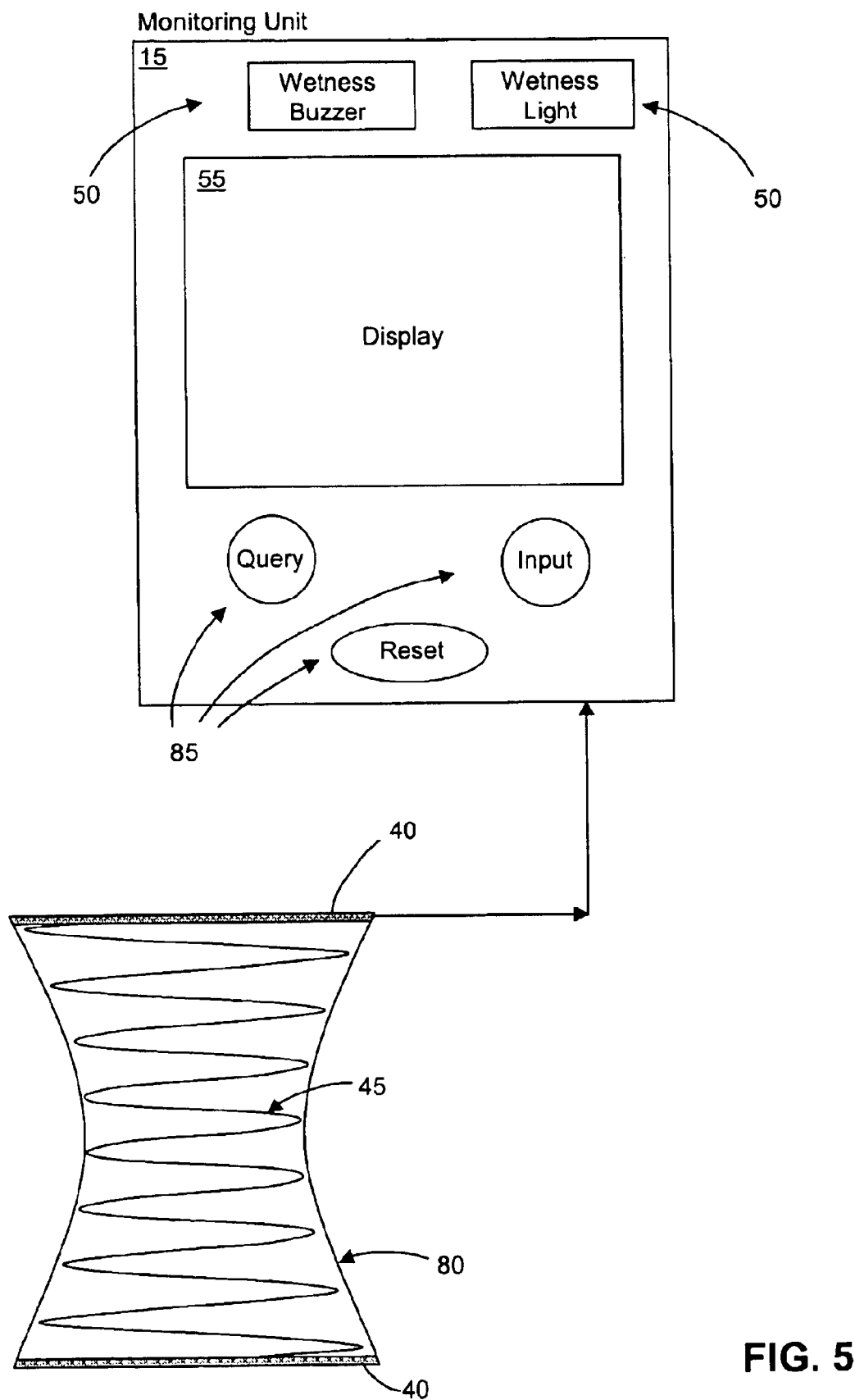
FIG. 5 is a diagram of a monitoring system having several integrated features in accordance with some embodiments of the present invention.

FIG. 5 is a diagram of a monitoring system having several integrated features in accordance with some embodiments of the present invention. As shown, a monitoring unit 15 generally includes a display unit 55, sensory alarms 50, and a user interface 85. The monitoring unit 15 is shown in communication with diaper 80 and associated human life and wetness sensors 40, 45.

Sensory alarms 50 are shown implemented as a wetness buzzer and light, but additional or fewer sensory alarms may be used as desired. The user interface 85 may also include any of a variety of useful devices that permits or facilitates user/system interaction. Typical user interfaces include, for example, facilities enabling one to retrieve person care data, activate/deactivate the monitoring system, and the like. In some implementations, a predetermined or user definable pass code may be required to access one or more functions of the monitoring system. Utilization of a pass code is useful for those who wish to use the system to reliably monitor the level of care provided by a caregiver. Since the pass code may be known only to the parent, the caregiver may not be able to readily access data acquired by the system, thus preventing system tampering by, for example, a caregiver wishing to conceal improper or negligent care.

Figure 6:
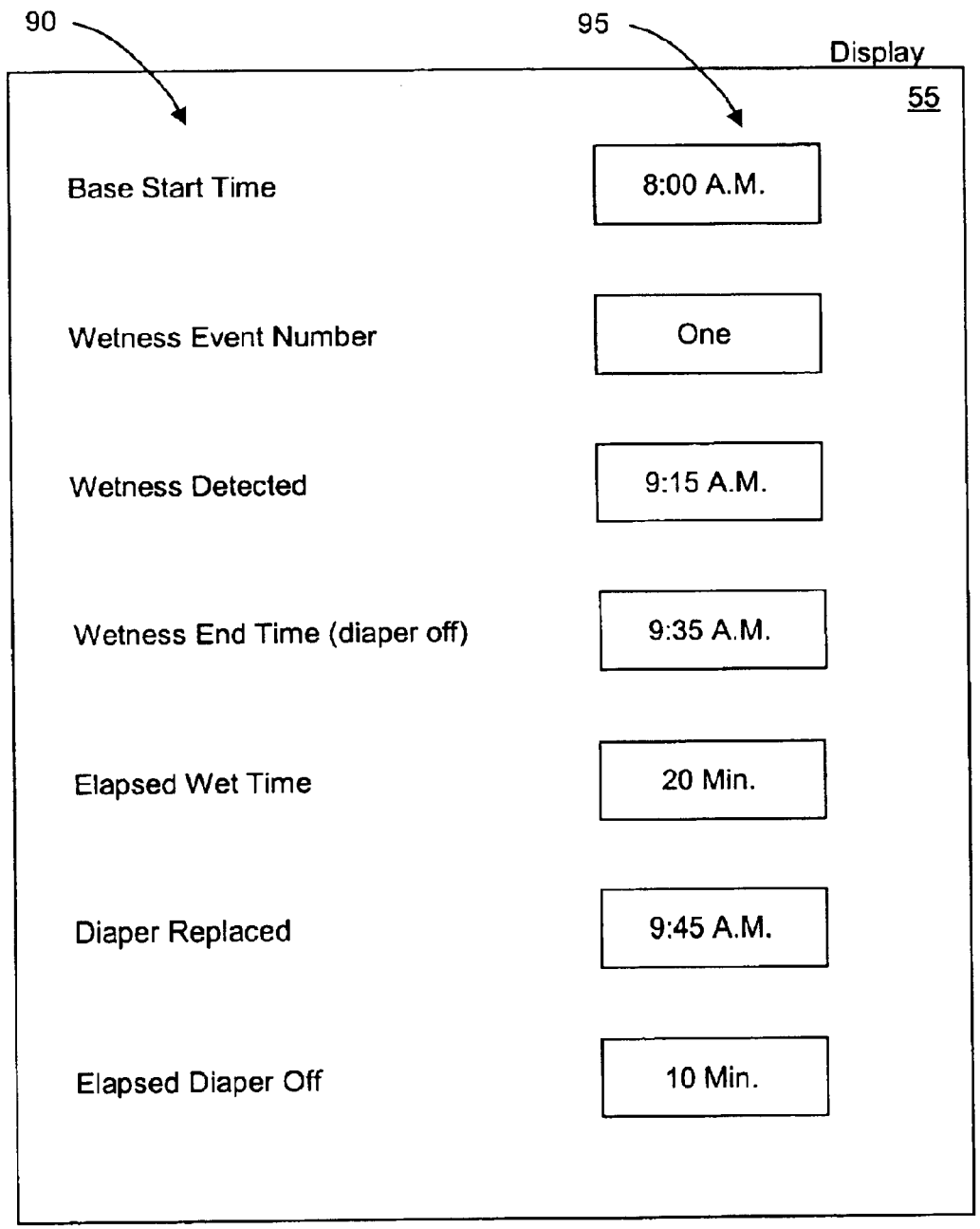
FIG. 6 is a diagram showing one of the many configurations possible for implementing a display unit in accordance with the present invention.

FIG. 6 shows one of the many configurations possible for implementing display unit 55 in accordance with the present invention. It is to be understood while the illustrated features are representative of typical implementations, no particular feature, or configuration of features, is essential or required.

In some embodiments, display unit 55 may generally include a series of events 90 and associated data displays 95. The series of events 95 relate to events that a user may desire tracking so that personal care of an individual may be monitored or assessed. FIG. 6 provides a representative list of the many possible events that may be tracked and monitored in accordance with the invention, but additional or fewer events may be tracked if desired.

The base start time may be used to indicate when the monitoring system has been activated. An example of system activation may be when care of an infant is turned over to a caregiver. In this scenario, the parent may activate the system by, for example, entering a required pass code. As indicated in FIG. 6, the monitoring system was activated at 8:00 A.M.

A wetness indicator may be used to track data associated with one or more wetness events. For example, it is not uncommon for an infant of have many wetness events over the course of a typical day. As such, a parent may want to track the quality of care provided by the caregiver for each of these wetness events. The first wetness event is depicted in this Figure.

The time of occurrence of a wetness event and when the diaper is eventually changed can also be displayed. In the example, a wetness event was detected at 9:15 A.M., and the diaper was changed at 9:35 A.M., indicating that the infant remained in a wet diaper for 20 minutes. This caregiver replaced the diaper at 9:45 A.M., resulting in the infant being without a diaper for 10 minutes. Excessive elapsed wet time or excessive diaper off time may indicate negligent care provided by the caregiver.

The display unit 55 may be formed using any suitable display technology (e.g., LCD, LED). In some embodiments, a single display is utilized, while in other embodiments some or all of the events 95 may include individual display units. Still further implementations for display unit 55 have been described with respect to FIG. 1C.

FIG. 7 is an example of the types of data that may be acquired and provided in accordance with the invention. This data is referred to generally as a personal care event log, and may be stored and retrieved using any of the aforementioned memory devices shown and described in FIGS. 1A–1C.

As depicted in FIG. 7, a personal care event log may include, for example, data associated with a number of wetness events and associated "diaper off" instances. The personal care event log is shown with data relating to three separate wetness events, and is capable of supporting data associated with up to N distinct wetness events. Typically, the personal care data log contains wetness event data information relating to a single day, but may easily be adapted to include data over several weeks or even months.

As indicated in the event log, the caregiver appeared to be relatively diligent in providing care to the infant for the first two wetness events, but then failed miserably in the third wetness event. For example, during the first two wetness events, the infant remained in a wet diaper for 20 minutes and 6 minutes, respectively. Thus, it appears that the caregiver is proving an acceptable level of care. However, after the third wetness event (11:42 A.M.), the infant remained in wet diaper for 126 minutes (until 1:48 P.M.), thus indicating negligence and lack of care provided to the infant.

Figure 8:
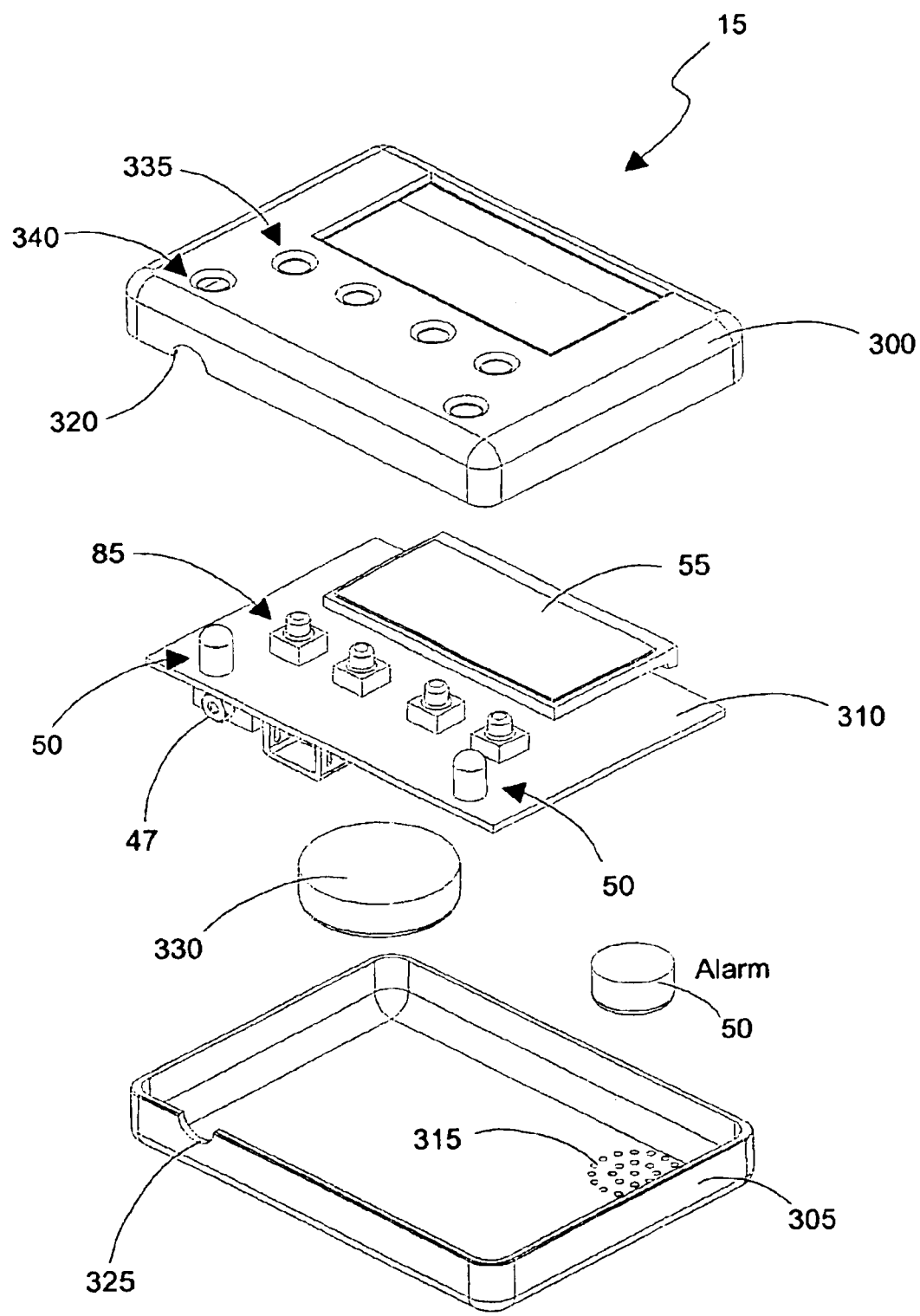
FIG. 8 is an exploded perspective view of an exemplary monitoring unit in accordance with some embodiments of the invention.

FIG. 8 is an exploded perspective view of an exemplary monitoring unit in accordance with some embodiments of the invention. Monitoring unit 15 is shown having upper and lower housings 300, 305 which may be used to contain an electronics module 310. The electronics module 310 is shown having sensor port 47, several sensory alarms 50, a display unit 55, and a user interface 85. Access to the sensor port 47 is facilitated by port cut-outs 320, 325 respectively formed in upper and lower housings 300, 305.

Sensory alarms 50 are shown implemented as a wetness alarm and two individual LEDs attached to an upper surface of the electronics module 310. If desired, auditory holes 315 may be formed in the lower housing 305, proximate to the wetness buzzer 50, to facilitate sound propagation.

The user interface 85 is shown implemented as four discrete buttons formed on the electronics module 310. Access to the user interface 85, once assembled, may be accomplished via user interface cut-outs 335 formed on the upper housing 300. Similarly, LED cut-outs 340 may be used to expose LED sensory alarms 50. The monitoring unit 15 may be powered by any suitable power source, such as battery 330. Again, the monitoring unit shown in FIG. 8 is but one example of the many possible implementations and embodiments of the invention, and is shown having many optional features that are not required or essential.

Figure 9A:
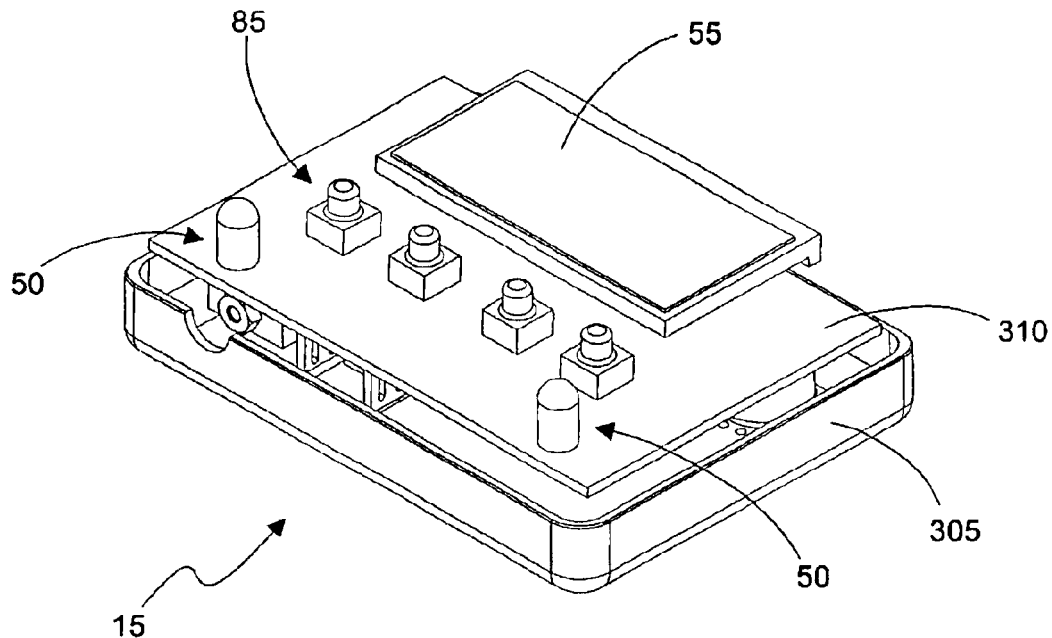
FIGS. 9A and 9B are perspective views showing, respectively, partially assembled and assembled views of the exemplary monitoring unit of FIG. 8.
Figure 9B:
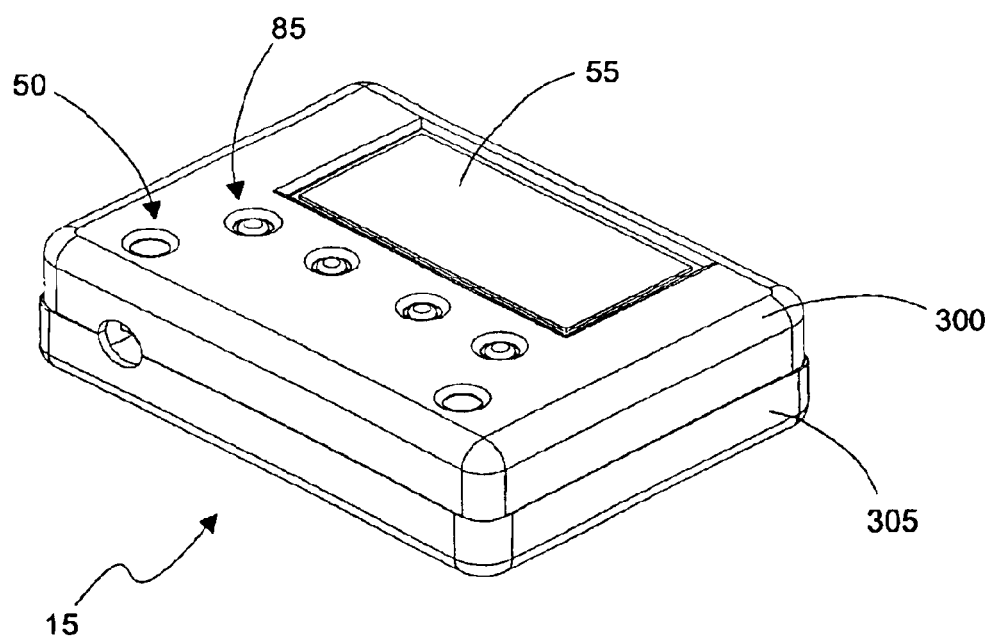

FIGS. 9A and 9B are perspective views showing, respectively, partially assembled and assembled views of the exemplary monitoring unit of FIG. 8. In FIG. 9A, the electronics module 310 is shown positioned within the lower housing 305. FIG. 9B depicts the monitoring unit 15 as it may appear after assembly.

Figure 10A:
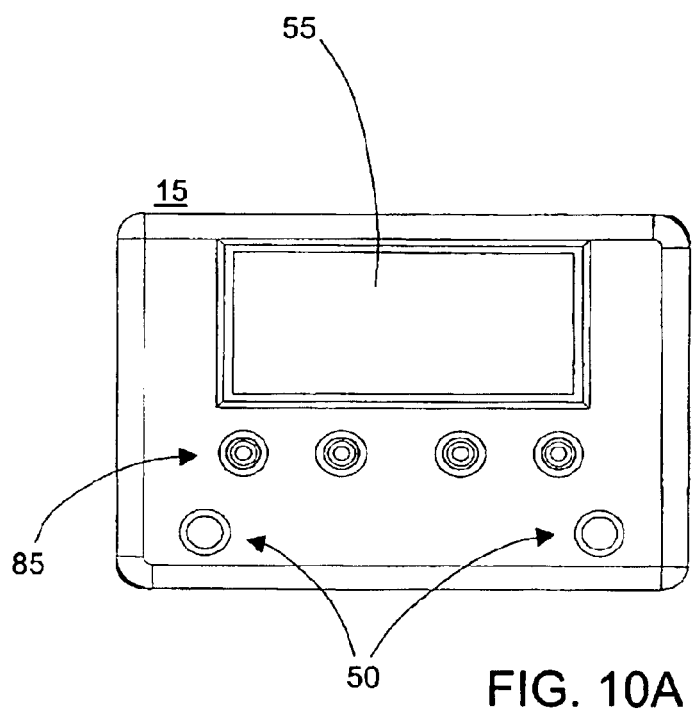
FIGS. 10A through 10C are top, front, and side views, respectively, of an assembled monitoring unit of FIG. 8.
Figure 10B:
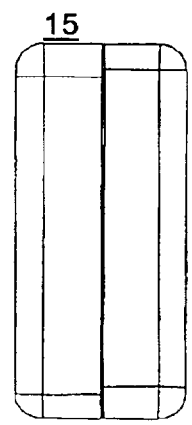
Figure 10C:
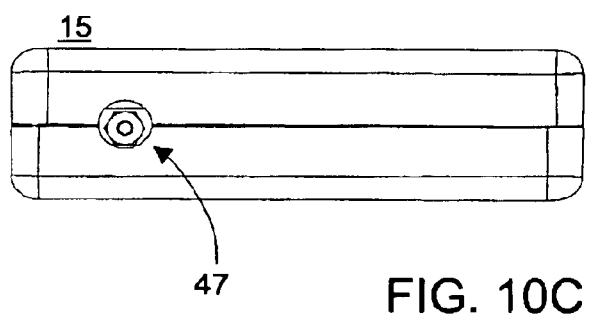

FIGS. 10A through 10C are top, front, and side views, respectively, of an assembled monitoring unit of FIG. 8. These Figures provide an illustration of the relative relationship of some of the features that may be included with the monitoring unit 15. For example, the sensory alarms 50 (e.g., LEDs), display unit 55, and user interface 85 buttons can be seen in the top view of FIG. 10A, while the sensor port 47 is viewable in the front view of FIG. 10C.

An appropriately configured personal care monitoring system may be utilized or implemented in a variety of different manners including child care facilities, hospitals, nursing homes, private home care, "nanny watch" services, remote monitoring systems, and the like. Those who may also benefit from the use of such systems include concerned parents, healthcare industries, medical and hospital organizations, as well as those providing convalescent and hospice care.

While the invention has been described in detail with reference to disclosed embodiments, various modifications within the scope and spirit of the invention will be apparent to those of working skill in this technological field. It is to be appreciated that features described with respect to one embodiment typically may be applied to other embodiments. Therefore, the invention properly is to be construed with reference to the appended claims.

What is claimed is:

1. A personal care monitoring system comprising:
    a wetness sensor configured to detect a wetness event occurring within an associated diaper;
    a human life sensor configured to detect a presence or absence of human life relative to said associated diaper; and
    a monitoring unit comprising a system controller in communication with said wetness and human life sensors, wherein said system controller monitors said wetness and human life sensors and generates data associated with detected wetness events and the presence or absence of human life relative to said associated diaper.

2. The personal care monitoring system according to claim 1, said system further comprising:
    a display unit configured with said monitoring unit and in communication with said system controller, wherein said display unit is adapted to display said generated data.

3. The personal care monitoring system according to claim 1, said system further comprising:
    an external display unit adapted to display said generated data; and
    a wireless transmitter configured with said monitoring unit and in communication with said system controller, wherein said wireless transmitter facilitates communications between said monitoring unit and said external display unit, wherein said communications include said generated data.

4. The personal care monitoring system according to claim 3, wherein said wireless transmitter facilitates communications between said monitoring unit and an external sensory alarm, wherein said external sensory alarm is responsive to a detection of a wetness event.

5. The personal care monitoring system according to claim 1, said system further comprising:
    removable memory configured with said monitoring unit and in communication with said system controller, wherein said removable memory comprises said generated data.

6. The personal care monitoring system according to claim 5, wherein said removable memory is a memory type selected from the group consisting of electrically erasable programmable read-only memory (EEPROM), erasable programmable read-only memory (EPROM), programmable read-only memory (PROM), read-only memory (ROM), magnetic memory, and flash memory.

7. The personal care monitoring system according to claim 1, said system further comprising:
    a data port configured with said monitoring unit and in communication with said system controller, wherein said data port facilitates communications between said monitoring unit and an external system, wherein said communications include said generated data.

8. The personal care monitoring system according to claim 1, wherein said wetness and human life sensors are integrated into a single sensor device.

9. The personal care monitoring system according to claim 1, wherein said life sensor is a sensor selected from the group consisting of a heat sensor, salinity sensor, heart rate monitor, conductance device, and a pH measuring device.

10. The personal care monitoring system according to claim 1, wherein said wetness sensor is a sensor selected from the group consisting of a hydrogen ion sensor, urea sensor, pH measuring device, and an ammonia sensor.

11. The personal care monitoring system according to claim 1, wherein said wetness and human life sensors are at least partially embedded within said associated diaper.

12. The personal care monitoring system according to claim 1, wherein said wetness and human life sensors are disposed onto said associated diaper.

13. The personal care monitoring system according to claim 1, wherein said wetness sensor comprises a wire mesh at least partially embedded within said associated diaper.

14. The personal care monitoring system according to claim 1, wherein said associated diaper is a disposable diaper; and
wherein said wetness and human life sensors are at least partially embedded within said associated disposable diaper.

15. The personal care monitoring system according to claim 1, said system further comprising:
a sensory alarm configured with said monitoring unit and in communication with said system controller, wherein said sensory alarm is responsive to a detection of a wetness event.

16. A wearable article operable with a personal care monitoring system, said article comprising:
a diaper comprising a liquid impermeable layer having an interior surface and an exterior surface;
a wetness sensor configured with said diaper, wherein said wetness sensor is adapted to detect a wetness event occurring within said diaper;
a human life sensor configured with said diaper, wherein said human life sensor is adapted to detect a presence or absence of human life relative to said diaper; and
wherein said wetness and human life sensors are adapted to responsively communicate to an associated personal care monitoring unit, detected wetness events and the presence or absence of human life relative to said diaper.

17. The article according to claim 16, wherein said personal care monitoring unit is detachably connected to said diaper.

18. The article according to claim 16, wherein said personal care monitoring unit is integrated with said diaper, and wherein said monitoring unit includes removable memory comprising data associated with said detected wetness events and the presence or absence of human life.

19. The article according to claim 16, wherein said removable memory is a memory type selected from the group consisting of electrically erasable programmable read-only memory (EEPROM), erasable programmable read-only memory (EPROM), programmable read-only memory (PROM), read-only memory (ROM), magnetic memory, and flash memory.

20. The article according to claim 16, wherein said wetness and human life sensors are integrated into a single sensor device.

21. The article according to claim 16, wherein said human life sensor is a sensor selected from the group consisting of a heat sensor, salinity sensor, heart rate monitor, conductance device, and a pH measuring device.

22. The article according to claim 16, wherein said wetness sensor is a sensor selected from the group consisting of a hydrogen ion sensor, urea sensor, pH measuring device, and a ammonia sensor.

23. The article according to claim 16, wherein said wetness and human life sensors are at least partially embedded within said interior surface of said diaper.

24. The article according to claim 16, wherein said wetness and human life sensors are disposed onto said interior surface of said diaper.

25. The article according to claim 16, wherein said diaper is a disposable diaper; and
wherein said wetness and human life sensors are at least partially embedded within said interior surface of said disposable diaper.

26. The article according to claim 16, wherein said diaper is a disposable diaper; and
wherein said wetness and human life sensors are disposed onto said interior surface of said associated disposable diaper.

27. A personal care monitoring system comprising:
means for detecting a wetness event occurring within an associated diaper;
means for detecting a presence or absence of human life relative to said associated diaper; and
means for monitoring and controlling said wetness event detecting means and said presence of human life detecting means, wherein said monitoring and controlling means generates data associated with detected wetness events and the presence or absence of human life relative to said associated diaper.

28. The personal care monitoring system according to claim 27, said system further comprising:
displaying means configured with said monitoring and controlling means, wherein said means for displaying is adapted to display said generated data.

29. The personal care monitoring system according to claim 27, said system further comprising:
external display means for displaying said generated data; and
wireless transmission means for facilitating communications between said monitoring unit means and said external display means, wherein said communications include said generated data.

30. The personal care monitoring system according to claim 27, said system further comprising:
removable memory means configured with said monitoring and controlling means, wherein said removable memory means comprises said generated data.

31. The personal care monitoring system according to claim 27, said system further comprising:
data port means configured with said monitoring and controlling means, wherein said data port means facilitates communications between said monitoring and controlling means and an external system, wherein said communications includes said generated data.

32. The personal care monitoring system according to claim 27, wherein said wetness event detecting means and said presence of human life detecting means are at least partially embedded within said associated diaper.

33. The personal care monitoring system according to claim 27, wherein said wetness event detecting means and said presence of human life detecting means are disposed onto said associated diaper.

34. A personal care monitoring system comprising:
a wetness sensor configured to detect a wetness event occurring within an associated diaper;
a human life sensor configured to detect a presence or absence of human life relative to said associated diaper;
a monitoring unit comprising a system controller in communication with said wetness and human life sensors, wherein said system controller monitors said wetness and human life sensors and generates data associated with detected wetness events and the presence or absence of human life relative to said associated diaper; and
a display unit configured with said monitoring unit and in communication with said system controller, wherein said display unit is adapted to display said generated data.

35. The personal care monitoring system according to claim 34, said system further comprising:

a sensory alarm configured with said monitoring unit and in communication with said system controller, wherein said sensory alarm is responsive whenever a threshold amount of time has elapsed where no presence of human life relative to said associated diaper has been detected by said human life sensor.

36. The personal care monitoring system according to claim 34, wherein said system controller responsively provides data to said monitoring unit indicative of any instances where no presence of human life relative to said associated diaper has been detected by said human life sensor.

37. The personal care monitoring system according to claim 34, said system further comprising:

a user interface configured with said monitoring unit and facilitating retrieval of said generated data.

* * * * *